(12) United States Patent
Hale

(10) Patent No.: US 7,449,329 B2
(45) Date of Patent: Nov. 11, 2008

(54) BLOOD TEST KIT

(76) Inventor: Anne S. Hale, 802 S. Clinton St., Stockbridge, MI (US) 49285

( * ) Notice: Subject to any disclaimer, the term of this patent is extended or adjusted under 35 U.S.C. 154(b) by 357 days.

(21) Appl. No.: 11/395,938

(22) Filed: Mar. 31, 2006

(65) Prior Publication Data

US 2007/0231834 A1 Oct. 4, 2007

(51) Int. Cl.
*G01N 33/558* (2006.01)
*G01N 33/538* (2006.01)

(52) U.S. Cl. .................. 435/288.6; 422/58; 422/59; 422/61; 422/68.1; 422/72; 422/73; 422/101; 435/7.24; 435/7.25; 435/287.2; 435/288.1; 435/810; 436/514; 436/518; 436/519; 436/520; 436/524; 436/527; 436/528; 436/529; 436/531; 436/534; 436/536; 436/538; 436/541; 436/810

(58) Field of Classification Search .................. None
See application file for complete search history.

(56) References Cited

U.S. PATENT DOCUMENTS

| | | | |
|---|---|---|---|
| 5,338,689 A | 8/1994 | Yves et al. | |
| 5,460,940 A | 10/1995 | Yves et al. | |
| 5,512,432 A | 4/1996 | Lapierre et al. | |
| 5,552,064 A | 9/1996 | Chachowski et al. | |
| 5,665,558 A | 9/1997 | Frame et al. | |
| 5,780,248 A | 7/1998 | Milchanoski et al. | |
| 5,863,802 A | 1/1999 | Yves et al. | |
| 5,905,028 A | 5/1999 | Frame et al. | |
| 6,114,179 A | 9/2000 | Lapierre et al. | |
| 2004/0166551 A1* | 8/2004 | Moulds et al. | ........ 435/13 |

* cited by examiner

*Primary Examiner*—Christopher L Chin
(74) *Attorney, Agent, or Firm*—Mary M. Moyne; Fraser Trebilcock Davis & Dunlap, P.C.

(57) ABSTRACT

A blood crossmatching apparatus, kit and methods for testing the compatibility of mammals for blood transfusion. Particulate layers in the apparatus allow nonagglutinated red blood cells to permeate through, while agglutinated red blood cells cannot. The apparatus also has a density solution layered above particulate layers. The density solution separates white blood cells from red blood cells in the whole blood when centrifuged, without lysing the red blood cells. Thus, the apparatus can be used to test whole blood.

13 Claims, 6 Drawing Sheets

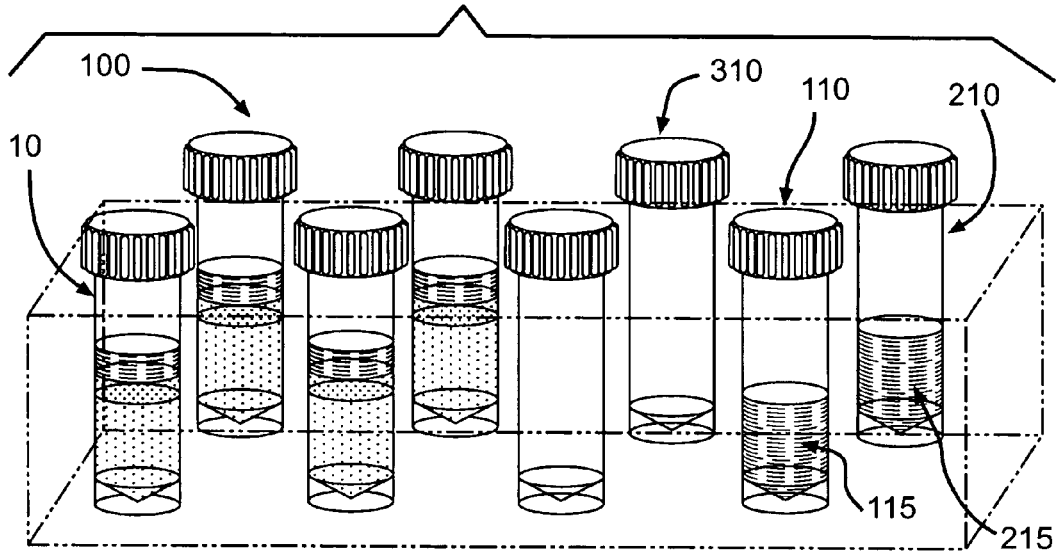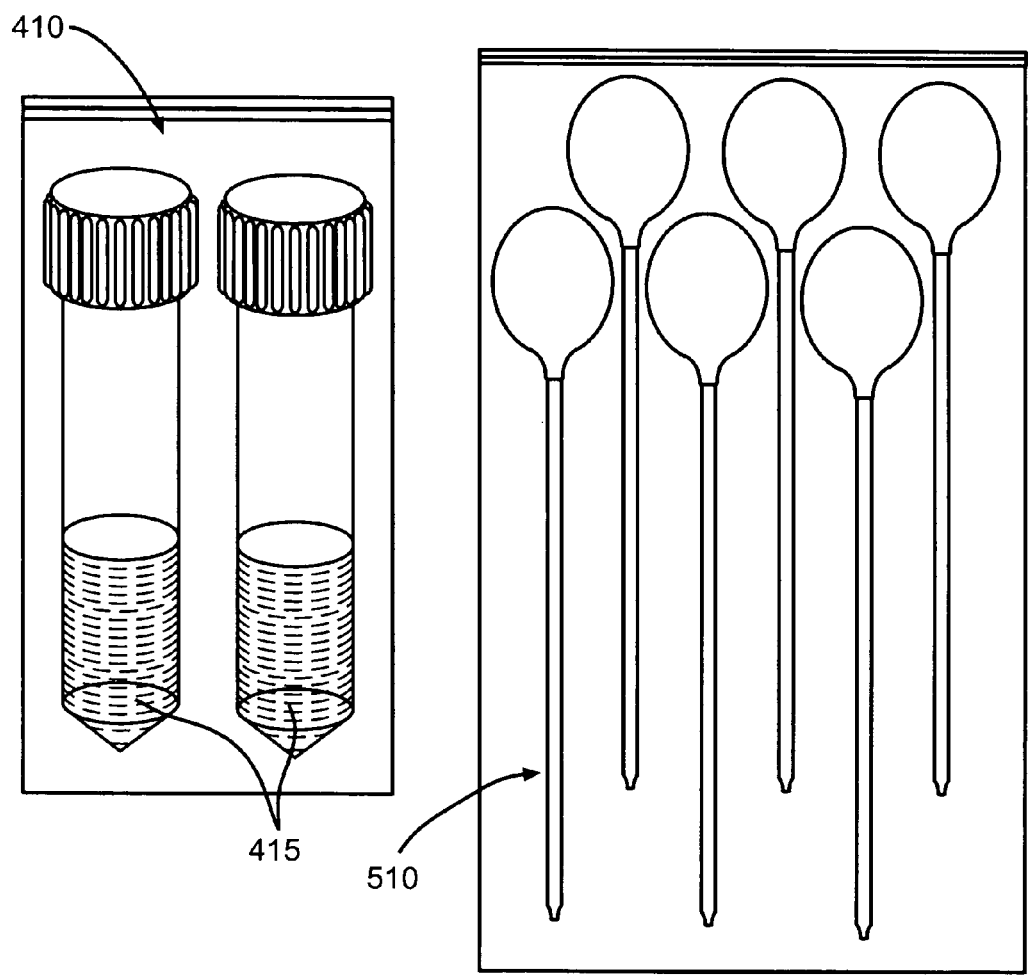
FIG.4

BLOOD TEST KIT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION (1) Field of the Invention

The present invention relates, in general, to agglutination assays. Specifically, the present invention relates to a blood crossmatching apparatus, methods and kits for determining whether mammals are compatible for blood transfusion.

(2) Description of the Related Art

Currently, field veterinarians do not have access to an easy to use, accurate means of evaluating a donor and recipient pair for possible transfusion reactions. Tube agglutination assays are currently used prior to blood transfusion, however these assays are cumbersome and involve erythrocyte preparation and long incubation times. These assays may not always lead to consistent results depending upon the experience of the technician. Additionally, some veterinarians do not have access to a laboratory qualified to perform agglutination assays. Therefore, it would be desirable that a test is available that is quick and simple to use.

Some advancements have been made in the field. U.S. Pat. Nos. 5,338,689, 5,460,940, and 5,863,802 all to Yves et al., and U.S. Pat. Nos. 5,512,432 and 6,114,179 both to Lapierre et al. disclose a method of detecting a target antibody or an antigen on a colored carrier such as an erythrocyte. The method of detection is based upon centrifugation in the presence of inert particles. The inert particles can be cross-linked polymers such as agarose including commercially available particles such as Sepharose® particles. The carrier-bound antigens (ie. erythrocyte antigens) and antibodies have different centrifugation properties than antigen-antibody complexes. If an antigen-antibody complex on a carrier is centrifuged, the carrier-bound complex lies on the inert particles. If no reaction has taken place, the antigen or antibody will pass through the layer of inert particles and come to rest under the particles. Weakly positive reactions may also occur, in which case the carrier-bound antigen-antibody complex is situated within the layer of inert particles.

U.S. Pat. Nos. 5,665,558 and 5,905,028 both to Frame et al. disclose an indirect assay where erythrocytes are exposed to serum antibodies and the mixture is incubated to bind the antibodies to the erythrocytes. In compatibility testing, donor erythrocytes are used in combination with a serum specimen from a patient or donor. If the donor's serum specimen contains IgG antibodies directed against an antigen present on the erythrocytes used in the test, the erythrocytes will adhere to Protein G as a ligand on particles at the top of the matrix. In the case of a weak antigen-antibody reaction, some erythrocytes will adhere to the Protein G agarose particles at the top of the matrix and some will collect at the bottom of the reaction tube. If the serum specimen does not contain antibodies to the antigens present on the erythrocytes, all the erythrocytes will collect at the bottom of the reaction tube. The ligand on the particles can be those known to bind immunoglobulin, such as Protein A, Protein G and Protein A/G.

While the related art teach blood crossmatching kits, there still exists a need for an improved blood crossmatching apparatus that can use whole blood for testing.

SUMMARY OF THE INVENTION

The present invention provides a blood crossmatching apparatus, methods and kit for testing the compatibility of mammals for blood transfusion. The apparatus can test a sample of whole blood. The apparatus has a density solution layered above particulates. The density solution separates white blood cells from red blood cells in the whole blood when centrifuged, while not lysing the red blood cells (erythrocytes). White blood cells can interfere in agglutination assays and cause false positives. Thus, the crossmatching apparatus can use whole blood to test the compatibility of the donor and recipient mammals for blood transfusion.

The methods of the present invention are dependent upon the antigen antibody interaction of the donor and the recipient blood. The first particulate layer excludes molecules or antigen antibody complexes greater than four million Daltons (4,000,000 Da). Thus the gel particulates act a sieve, catching large particles in the upper portion of the gel. U.S. Pat. Nos. 5,338,689, 5,460,940, and 5,863,802 all to Yves et al., and U.S. Pat. Nos. 5,512,432 and 6,114,179 both to Lapierre et al., hereby incorporated herein by reference in their entirety describe a method of detecting antigens and/or antibodies using inert particles. U.S. Pat. Nos. 5,665,558 and 5,905,028 both to Frame et al., hereby incorporated herein by reference in their entirety, describe methods and apparatus for detecting bloodgroup antigens and antibodies using immunoreactive particles.

Some unique aspects of the present invention are that the particulate gel matrix can be used to test lower mammals, despite the smaller size of subhuman erythrocytes. Additionally, the density solution and Protein A act to impede the sedimentation of white blood cells and larger proteins such that this test is able to use whole blood instead of washed red blood cells without these components of blood interfering with the test. The particulate matrix of the first layer is not a slurry but a packed particulate agarose gel. The methods of the present invention are dependent on the solid phase packed particulate nature of this gel. In addition, the unique positive control solution comprises antibodies that have been developed by alloimmunization of goats. Therefore, the positive control solution antibodies that are produced in this fashion can recognize canine, feline, equine, bovine and other lower mammalian red blood cells. Finally, centrifugation is performed in a standard benchtop centrifuge at about 500×g to about 700×g, and the centrifugation does not require a fixed rotor. The structure of the particulate layers and the method of formation of the layers allows for settling which provides more structure which allows the use of high centrifugation speeds.

Thus, the present invention provides a blood crossmatching apparatus for testing compatibility of mammals for blood transfusion using a sample of whole blood comprising: a centrifugeable tube having an open top end and an opposed closed bottom end; a first layer of particulates at the bottom end in the centrifugeable tube having a permeability enabling nonagglutinated red blood cells of compatible mammals to pass through the layer; a second layer of particulates layered upon the first layer in the centrifugeable tube, wherein particulates of the second layer comprise an immunoglobulin ligand bound to the particulates for bridging weakly agglutinating red blood cells; and a density solution layered into the centrifugeable tube over the second layer, wherein the density solution separates white blood cells from red blood cells in the whole blood when centrifuged, such that the apparatus can show an incompatibility of the mammals for blood transfusion as a red blood cell band on or in an upper portion of the first layer.

In some embodiments, the centrifugeable tube is a microcentrifuge tube. In further embodiments, the microcentrifuge tube is a 2 mL or a 1.5 mL microcentrifuge tube. In further embodiments, the first layer of particulates comprise 6% agarose particles. In still further embodiments, the first layer of particulates comprise Sepharose 6B® particles. In some embodiments, the second layer of particulates comprise 250 micron (μm) acrylic beads In further embodiments, the density solution comprises an aqueous glycerol solution. In still further embodiments, the aqueous glycerol solution comprises a 97% v/v glycerol solution. In still further embodiments, the immunoglobulin ligand is Protein A. In still further embodiments, the density layer has a depth from about 0.05 mm to about 1.5 mm.

The present invention provides a blood crossmatching apparatus for testing compatibility of mammals for blood transfusion using a sample of whole blood comprising: (a) a centrifugeable tube having an open top end and an opposed closed bottom end; (b) a first layer comprising particulates at the bottom end in the centrifugeable tube having a permeability enabling nonagglutinated red blood cells of compatible mammals to pass through the layer; (c) a second layer comprising a density solution layered into the centrifugeable tube over the first layer, wherein the density solution separates white blood cells from red blood cells in the whole blood when centrifuged; and (d) a third layer layered upon the second layer comprising an immunoglobulin ligand in aqueous solution for bridging weakly agglutinating red blood cells, such that the apparatus can show an incompatibility of the mammals for blood transfusion as a red blood cell band on or in an upper portion of the first layer.

The present invention provides a method of making a blood crossmatching apparatus for testing compatibility of mammals for blood transfusion using a sample of whole blood comprising the steps of: providing a centrifugeable tube having an open top end and an opposed closed bottom end; forming a first layer of particulates at the bottom end in the centrifugeable tube; forming a second layer of particulates upon the first layer in the centrifugeable tube, wherein particulates of the second layer comprise an immunoglobulin ligand bound to the particulates; and layering a density solution over the second particulate layer, wherein the density solution separates white blood cells from red blood cells in the whole blood when centrifuged so that the crossmatching apparatus can use whole blood to test the compatibility of the mammals for blood transfusion.

In further embodiments, the method further comprises incubating the centrifugeable tube at 4-6° C. for twelve to twenty four (12-24) hours after forming a first layer of particulates. In further embodiments, the method further comprises bringing the centrifugeable tube to room temperature after incubating. In further embodiments, the method further comprises incubating the centrifugeable tube for thirty (30) minutes after forming the second layer of particulates upon the first layer. In further embodiments, the method further comprises incubating the centrifugeable tube at 4-6° C. for twenty four to thirty six (24-36) hours after layering the density solution over the second particulate layer.

In some embodiments of the method, the centrifugeable tube is a microcentrifuge tube or a micro-hematocrit capillary tube. In further embodiments, the microcentrifuge tube is a 2 mL or a 1.5 mL microcentrifuge tube. In further embodiments, the first layer of particulates comprise 6% agarose particles. In still further embodiments, the first layer of particulates comprise Sepharose 6B® particles. In some embodiments, the second layer of particulates comprise 250 micron (μm) acrylic beads In further embodiments, the density solution comprises an aqueous glycerol solution. In still further embodiments, the aqueous glycerol solution comprises a 97% v/v glycerol solution. In still further embodiments, the immunoglobulin ligand is Protein A.

The present invention provides a method for testing the compatibility of donor and recipient mammals prior to blood transfusion comprising: providing a blood crossmatching apparatus for testing compatibility of mammals for blood transfusion using whole blood comprising a centrifugeable tube having an open top end and an opposed closed bottom end; a first layer of particulates at the bottom end in the centrifugeable tube having a permeability enabling nonagglutinated red blood cells of compatible mammals to pass through the layer; a second layer of particulates layered upon the first layer in the centrifugeable tube, wherein particulates of the second layer comprise an immunoglobulin ligand bound to the particulates; and a density solution layered into the centrifugeable tube over the second layer, wherein the density solution separates white blood cells from red blood cells in the whole blood when centrifuged; dispensing a mixture of the whole donor mammal blood and serum from a recipient mammal into the open top end of the centrifugeable tube of the crossmatching apparatus; centrifuging the blood crossmatching apparatus to provide a red blood cell band; and interpreting from a location of the red blood cell band above or below the first layer of particulates in the centrifugeable tube, the compatibility of the mammals for blood transfusion.

In some embodiments of the method, the blood crossmatching apparatus is centrifuged at a centrifugal force of about 500×g to 700×g. In some embodiments, the centrifugeable tube is a microcentrifuge tube or a micro-hematocrit capillary tube. In further embodiments, the microcentrifuge tube is a 2 mL or a 1.5 mL microcentrifuge tube. In further embodiments, the first layer of particulates comprise 6% agarose particles. In still further embodiments, the first layer of particulates comprise Sepharose 6B® particles. In some embodiments, the second layer of particulates comprise 250 micron (μm) acrylic beads In further embodiments, the density solution comprises an aqueous glycerol solution. In still further embodiments, the aqueous glycerol solution comprises a 97% v/v glycerol solution. In still further embodiments, the immunoglobulin ligand is Protein A.

The present invention provides a method for testing the compatibility of donor and recipient mammals prior to blood transfusion comprising: collecting whole blood from the donor and serum from the recipient; diluting the whole blood from the donor; providing a positive control solution and a negative control solution; mixing an aliquot of the diluted whole blood from the donor with the serum from the recipient to provide a sample; mixing an aliquot of the diluted whole blood from the donor with a positive control solution to provide a positive control mixture; mixing an aliquot of the diluted whole blood from the donor with a negative control solution to provide a negative control mixture; providing three blood crossmatching apparatuses, each apparatus comprising a centrifugeable tube having an open top end and an opposed closed bottom end; a first layer of particulates at the bottom end in the centrifugeable tube having a permeability enabling nonagglutinated red blood cells of compatible mammals to pass through the layer; a second layer of particulates layered upon the first layer in the centrifugeable tube, wherein particulates of the second layer comprise an immunoglobulin ligand bound to the particulates; and a density solution layered into the centrifugeable tube over the second layer, wherein the density solution separates white blood cells from red blood cells in the whole blood when centrifuged; dispensing an aliquot of the sample into the open top end of a first of the three blood crossmatching apparatuses to provide a sample test apparatus; dispensing an aliquot of the positive control mixture into the open top end of a second of the three blood crossmatching apparatuses to provide a positive control test apparatus; dispensing an aliquot of the negative control mixture into the open top end of a third of the three blood crossmatching apparatuses to provide a negative control test apparatus; centrifuging the three blood crossmatching apparatuses to provide red blood cell bands for each of the test apparatuses; interpreting the red blood cell bands of the negative control test apparatus and the positive control test apparatus to determine whether the method was properly performed; and interpreting from a location of the red blood cell band of the sample test apparatus above or below the first layer of particulates in the centrifugeable tube the compatibility of the mammals for blood transfusion.

In further embodiments of the method, the blood crossmatching apparatus is centrifuged at a centrifugal force of about 500×g to 700×g. In some embodiments, the centrifugeable tube is a microcentrifuge tube or a micro-hematocrit capillary tube. In further embodiments, the microcentrifuge tube is a 2 mL or a 1.5 mL microcentrifuge tube. In further embodiments, the first layer of particulates comprise 6% agarose particles. In still further embodiments, the first layer of particulates comprise Sepharose 6B® particles. In some embodiments, the second layer of particulates comprise 250 micron (μm) acrylic beads In further embodiments, the density solution comprises an aqueous glycerol solution. In still further embodiments, the aqueous glycerol solution comprises a 97% v/v glycerol solution. In still further embodiments, the immunoglobulin ligand is Protein A.

The present invention provides a blood crossmatching test kit for testing compatibility of mammals for blood transfusion using whole donor blood comprising: a blood crossmatching apparatus comprising a centrifugeable tube having an open top end and an opposed closed bottom end; a first layer of particulates at the bottom end in the centrifugeable tube having a permeability enabling nonagglutinated red blood cells of compatible mammals to pass through the layer; a second layer of particulates layered upon the first layer in the centrifugeable tube, wherein particulates of the second layer comprise an immunoglobulin ligand bound to the particulates for bridging weakly agglutinating red blood cells; and a density solution layered into the centrifugeable tube over the second layer, wherein the density solution separates white blood cells from red blood cells in the whole blood when centrifuged; a positive control solution that can agglutinate the blood of any species of mammal used for testing; and a negative control solution that cannot agglutinate the blood of any species of mammal used for testing.

In some embodiments, the blood crossmatching test kit further comprises one or more whole blood dilution tubes having a premeasured volume of low ionic strength saline (LISS) for diluting the whole donor blood. In still further embodiments, the blood crossmatching test kit further comprises one or more reaction tubes for mixing the donor blood and serum of a recipient. In further still embodiments, the blood crossmatching test kit further comprises one or more disposable pipets capable of dispensing drops having a 50 μL volume. In some embodiments, the centrifugeable tube is a microcentrifuge tube or a micro-hematocrit capillary tube. In further embodiments, the microcentrifuge tube is a 2 mL or a 1.5 mL microcentrifuge tube. In further embodiments, the first layer of particulates comprise 6% agarose particles. In still further embodiments, the first layer of particulates comprise Sepharose 6B® particles. In some embodiments, the second layer of particulates comprise 250 micron (μm) acrylic beads In further embodiments, the density solution comprises an aqueous glycerol solution. In still further embodiments, the aqueous glycerol solution comprises a 97% v/v glycerol solution. In still further embodiments, the immunoglobulin ligand is Protein A.

BRIEF DESCRIPTION OF THE DRAWINGS

FIG. 3A and FIG. 3B illustrate positive reactions, while FIG. 3C and FIG. 3D illustrate negative reactions.

FIG. 4 illustrates one embodiment of a blood crossmatching kit 100 of the present invention.

DETAILED DESCRIPTION OF THE INVENTION

Figure 1:
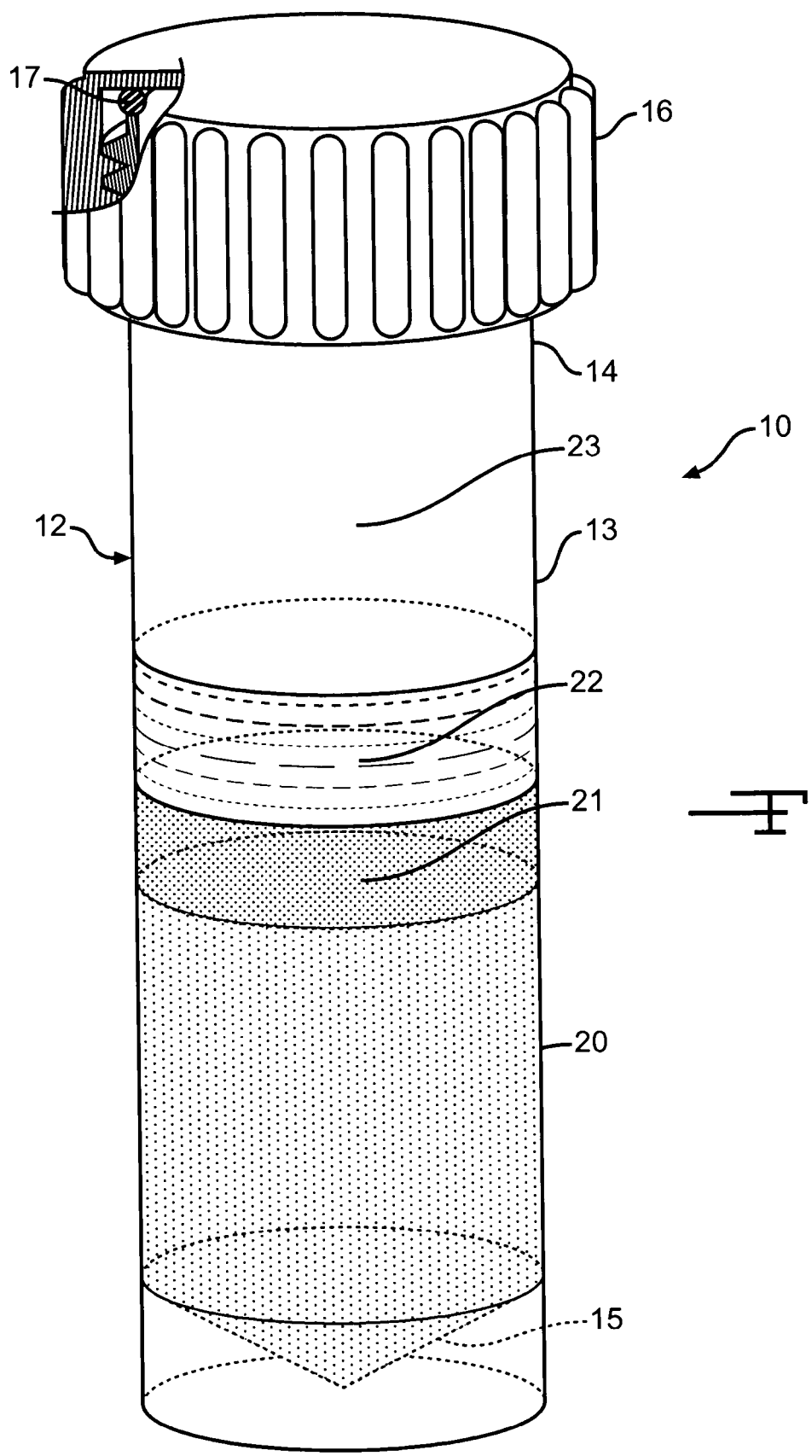
FIG. 1 illustrates one embodiment of a blood crossmatching apparatus 10 of the present invention.

All patents, patent applications, government publications, government regulations, and literature references cited in this specification are hereby incorporated herein by reference in their entirety. In case of conflict, the present description, including definitions, will control.

As used herein, the term "red blood cells" refers to erythrocytes.

As used herein, the term "mammals" refers to both humans and lower mammals. Lower mammals are mammals lower than a human (ie. subhuman). For example, the term includes companion animals such as dogs and cats, however the term is not limited to companion animals.

As used herein, the term "centrifugeable tube" refers to centrifuge tubes, such as any microcentrifuge tube known in the art, or hematocrit tubes, such as any micro-hematocrit capillary tubes known in the art.

As used herein, the term "particulate" refers to glass, acrylic, silica gel or any of a variety of polymer particulate including cross-linked polymers, such as, but not limited to agarose, polyacrylamide, polydextran, styrene-divinylbenzene, and methacrylate polymers and co-polymers. The term encompasses commercially available products such as Sephadex®, Sepharose®, Sephacryl® (GE Healthcare, Uppsala, Sweden), and Bio-Gel® (Bio-Rad Laboratories, Richmond, Calif.) particles. The particles can be a bead or other shape.

As used herein, the term "first layer of particulates" or "first particulate layer" refers to a layer of particulates having a spacing between the particulates such that the resulting permeability allows nonagglutinated erythrocytes of the mammal being tested to pass through the layer. In one embodiment the first layer of particulates is comprised of Sepharose® 6B beads. Thus, the layer excludes molecules and antigen-antibody complexes greater than 4,000,000 Daltons (Da), while allowing smaller materials, such as individual erythrocytes to permeate through the layer.

As used herein, the term "density solution" refers to any immunologically inert solution which has a density greater than water and which slows the sedimentation of white blood cells with respect to erythrocytes, while not causing lysis of the erythrocytes. One density solution is a high percentage aqueous glycerol solution. The aqueous glycerol solution can be between about 92 and 99 volume percent (% v/v) glycerol. One density solution that can be used is a ninety seven volume percent (97% v/v) aqueous glycerol solution. Some density solutions include glycerol or any other trihydric alchohol, or any $C_2$-$C_5$ ester with a density from about 1.2 grams per milliliter (g/ml) to about 1.3 grams per milliliter (g/ml). The pH of the density solution is compatible with the blood cells. The density layer has a depth of about 0.05 mm to about 1.5 mm when layered in the centrifuge tube.

Other density solutions encompassed by the present invention generally include, but are not limited to $C_2$-$C_8$ polyhydric alcohols. Some examples of density solutions include sorbitol solutions. Large polymer solutions, such as solutions comprising Ficoll® copolymer (GE Healthcare) can cause lysis of the erythrocytes (red blood cells). The term "density solution" is limited to density solutions that do not cause lysis of the erythrocytes. In addition, solutions having large and/or charged molecules, such as dextran and trephalose can interfere with the agglutination process. Some agglutination reactions only achieve a 2+ agglutination, and it is important not to pull apart and disrupt the agglutination reaction. Thus, the term "density solution" does not encompass such solutions as Ficoll® copolymer, dextran, or trephalose solutions. The density layer can enter crevices in the particulate layers, but it remains a separate layer and does not intermix with the particulates.

As used herein, the term "immunoglobulin ligand" refers to any ligand that binds immunoglobulin molecules and can be covalently coupled to the particulates, including, but not limited to Protein A, Protein G, and Protein A/G. Immunoglobulins of the recipient serum or donor blood can be bound by the immunoglobulin ligand. Consequently, the red or white blood cells that these immunoglobulins bind will be indirectly bound by the ligand. The immunoglobulin ligand (eg. Protein A) bridges immunoglobulin (eg. IgG, IgM) so as to enhance agglutination, especially with weak agglutination reactions. In an alternative embodiment, the immunoglobulin ligand is not bound to particulates, but rather is provided in an aqueous solution. The immunoglobulin ligand (eg. Protein A) can also interact with lymphocytes and proteins to reduce the amount of lymphocytes and proteins that enters the first layer of particulates.

As used herein, the term "second layer of particulates" refers to any layer of particulates capable of binding the immunoglobulin ligand, such as, but not limited to acrylic beads.

The present invention provides a blood crossmatching apparatus, kit and methods for testing the compatibility of mammals for blood transfusion. Particulate layers in the apparatus allow nonagglutinated red blood cells to permeate through, while agglutinated red blood cells cannot. The apparatus also has a density solution layered above the particulate layers. Each of the layers of the apparatus thereby remain separate and do not intermix. The density solution separates white blood cells from red blood cells in the whole donor blood when centrifuged, while not lysing the red blood cells (erythrocytes). The crossmatching apparatus can thereby use whole donor blood to test the compatibility of the donor and recipient mammals for blood transfusion. While the present invention can be used for major crossmatching using whole donor blood, it is to be understood that the apparatus of the present invention can also be used for minor crossmatching using whole recipient blood.

FIG. 1 illustrates one embodiment of a blood crossmatching apparatus 10 of the present invention. The blood crossmatching apparatus 10 can be used to test compatibility of mammals for blood transfusion using whole donor blood. The apparatus 10 is comprised of a centrifugeable tube, such as a microcentrifuge tube 12 for small samples, with an outer wall 13 having an open top end 14 (best seen with cap 16 removed in FIG. 2) and an opposed closed bottom end 15 defining an internal chamber 23. The bottom end 15 can be conical in shape to make viewing of any precipitated erythrocytes 42 (best seen in FIG. 3C) easier. In further embodiments of the apparatus 10, the centrifugeable tube can be a micro-hematocrit capillary tube. To construct the apparatus 10, a first layer of particulates 20 is layered at the bottom end 15 of the internal chamber 23 in the microcentrifuge tube 12. Next, a second layer of particulates 21 is layered upon the first layer 20 in the microcentrifuge tube 12. In one (1) embodiment, the second layer of particulates 21 is 250 micron (μm) acrylic beads. The particulates of the second layer 21 comprise an immunoglobulin ligand bound to the particulates. In one embodiment, the immunoglobulin ligand is Protein A. The Protein A enhances bridging between red blood cells with weak agglutination. The Protein A also interacts with white blood cells and large proteins (such as albumin) so as to help decrease the amount of white blood cells and protein that enters the first layer of particulates 20. Finally, a density solution 22 is layered over the second particulate layer 21 forming a third layer. In one (1) embodiment, the density solution 22 is an aqueous glycerol solution. However, other aqueous density solutions can be used. The density solution 22 separates white blood cells 41 from the erythrocytes 42 (ie. red blood cells) in the whole donor blood when the apparatus 10 is centrifuged. Therefore, the crossmatching apparatus 10 can use whole blood of the donor to test the compatibility of the mammals for blood transfusion. It is understood that the crossmatching apparatus 10 can use whole blood of the recipient and a minor crossmatch can be performed. In one (1) embodiment, the first layer of particulates 20, the second layer of particulates 21 and the density solution 22 remain as separate layers and do not intermingle during centrifugation. In one (1) embodiment, the density solution 22 does not permeate into the first layer of particulates 20. In the illustrated embodiment (best seen in FIG. 1), a screw cap 16 is provided with an o-ring 17 to seal the chamber 23 during centrifugation. Any commercially available microcentrifuge tube 12 can be used including, but not limited to, a Sarstedt® brand (Nümbrecht, Germany) microcentrifuge tube.

Figure 3:
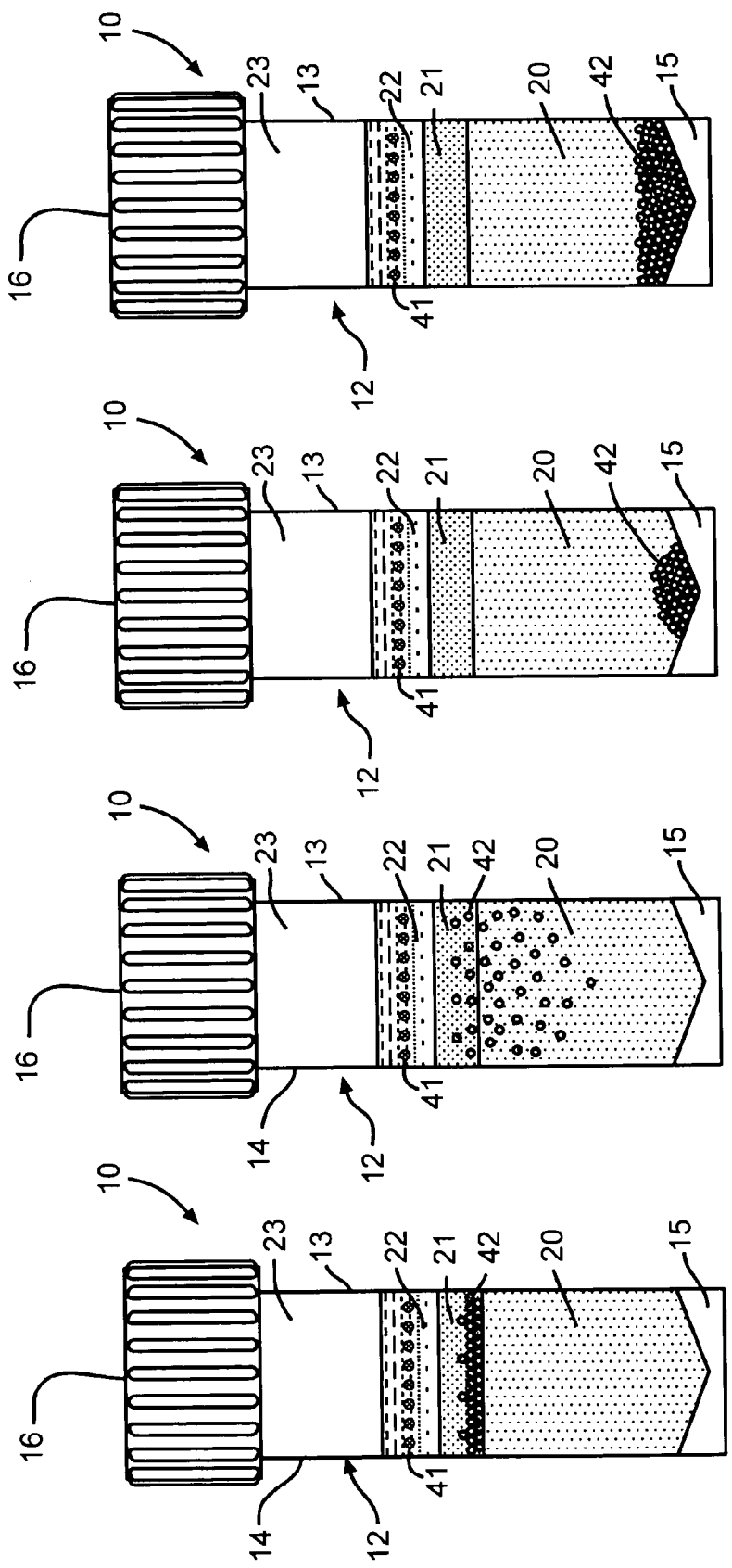
FIG. 3A through FIG. 3D are illustrations of the blood crossmatching apparatus 10 of FIG. 1 after centrifugation to provide various banding patterns of the donor white blood cells 41 (not visible with the naked eye) and erythrocytes 42.

In one embodiment, the first particulate layer 20 is comprised of 6% agarose particles, optionally Sepharose® 6B beads (GE Healthcare) on the bottom end 15 of the microcentrifuge tube 12. In one embodiment, the second particulate layer 21 is comprised of Protein A acrylic beads that are layered on top of the first particulate layer 20. Whole blood can be used with the crossmatching apparatus 10, so washing the erythrocytes is not required. The crossmatching apparatus 10 is dependent upon antigen-antibody interaction of the donor and recipient blood resulting in agglutination. The first particulate layer 20 excludes molecules and antigen-antibody complexes greater than 4,000,000 Daltons (Da) in the case of Sepharose® 6B beads. The first particulate layer 20 acts as a sieve, catching large particles in the upper portion of the first particulate layer 20. The crossmatching apparatus 10 is centrifuged in a standard benchtop centrifuge at a force of about 500×g to about 700×g and the resulting banding pattern is read by evaluating the position of the erythrocytes 42 in the microcentrifuge tube 12 after centrifugation (FIG. 3A). Positive crossreaction is indicated by a band of erythrocytes 42 on the top of the first particulate layer 20 or in the upper portion of the first particulate layer 20, while negative crossreaction is indicated by a band of erythrocytes 42 at the bottom end 15 of the microcentrifuge tube 12.

Figure 2:
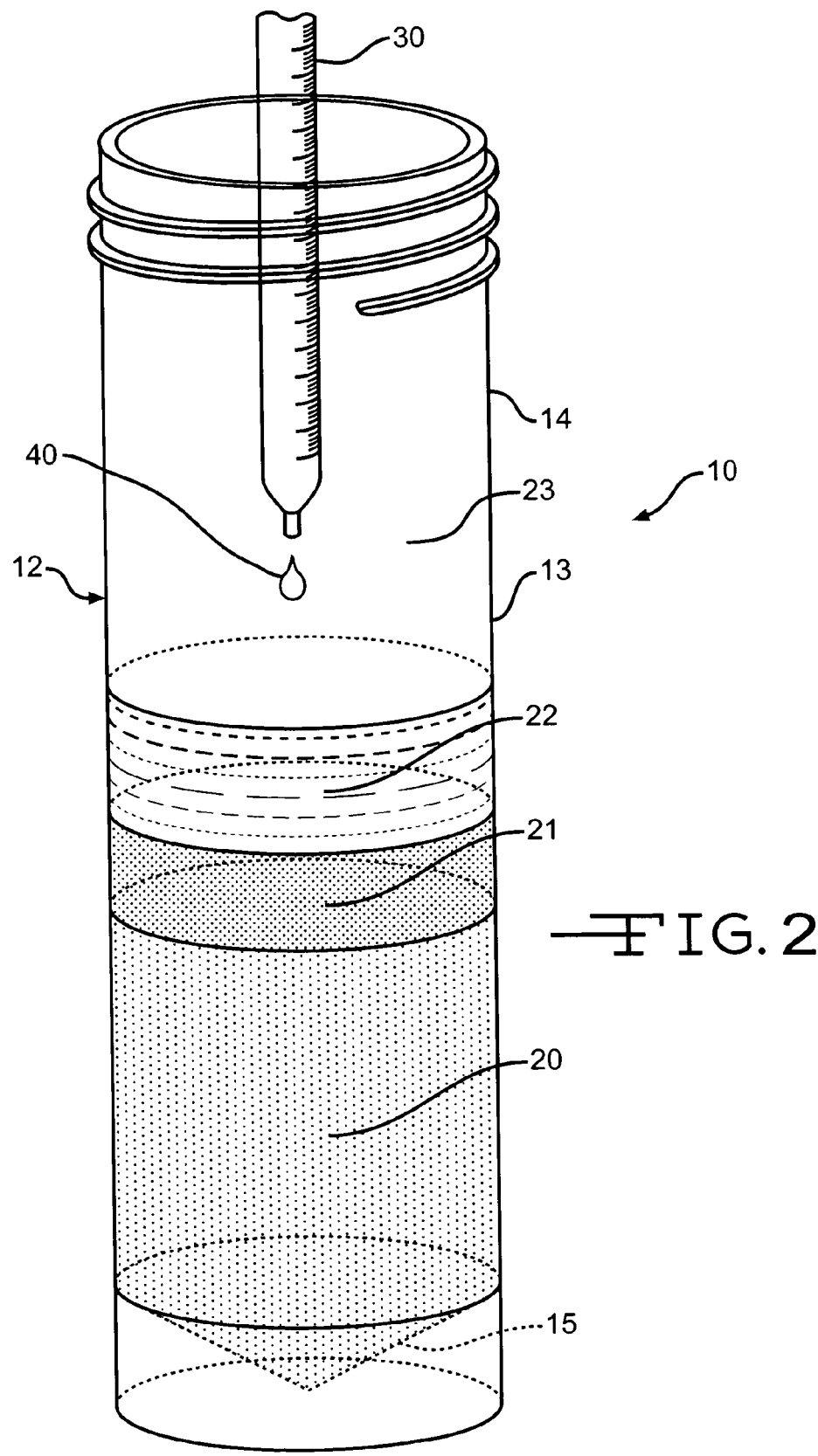
FIG. 2 is an illustration of diluted whole donor blood and recipient serum mixture 40 being dispensed into the blood crossmatching apparatus 10 of FIG. 1.

Thus, the crossmatching apparatus 10 allows for rapid compatibility testing between the donor and recipient mammal prior to transfusion. Whole EDTA treated blood from the donor is diluted in low ionic strength saline (LISS) at a 1:9 dilution. In a blank two milliliter (2 mL) microcentrifuge tube, 100 μLs of whole blood from the donor and 100 μLs of recipient serum is combined. A room temperature incubation of five minutes is performed. Fifty microliters (50 μL) of sample mixture 40 is transferred from the reaction tube to a blood crossmatching apparatus 10 after incubation. FIG. 2 illustrates a mixture 40 of the whole donor mammal blood and serum from the recipient mammal being transferred into the open top end 14 in the centrifuge tube 12 of the crossmatching apparatus 10 of FIG. 1 (with cap 16 removed). After loading the mixture 40 into the open top end 14 of the centrifuge tube 12 and onto the density solution 22 as illustrated in FIG. 2, the apparatus 10 is centrifuged at 500×g to about 700×g for 5-7 minutes. A majority of the white blood cells 41 do not pass through the density solution 22 as illustrated in FIG. 3A through FIG. 3D. The erythrocytes 42, however pass through the density solution 22 to form a banding pattern which depends upon the state of agglutination of the erythrocytes 42. The reaction is read by evaluating the position of the erythrocytes 42 in the tube 12 after centrifugation. FIG. 3A through FIG. 3D are illustrations of the blood crossmatching apparatus 10 of FIG. 1 after centrifugation with different sample mixtures added to provide various banding patterns of the donor erythrocytes 42. FIG. 3A and FIG. 3B illustrate positive reactions. Positive reactions are indicated by erythrocytes 42 on the top of the first particulate layer 20 (FIG. 3A) or in the upper third of the first particulate layer 20 (FIG. 3B). FIG. 3C and FIG. 3D illustrate negative reactions. Negative reactions are indicated by erythrocytes 42 in the bottom end 15 of the microcentrifuge tube 12 with no evidence of red blood cells (erythrocytes 42) left on the top of the first particulate layer 20 or in an upper third of the first particulate layer 20.

The apparatus 10 can be provided as a part of a blood crossmatching test kit 100 as illustrated in FIG. 4. At least one apparatus 10 is provided in the kit 100 along with a positive control tube 110 having positive control solution 115 that can agglutinate the blood of any species of mammal used (ie. a multispecies positive control) for testing. In one embodiment of the positive control solution 115, individual goats are immunized with one of the following antigens: feline type A red blood cells, feline type B red blood cells, canine type DEA 3,5 cells, bovine J positive red blood cells, or equine Ca positive red blood cells. Serum antibodies are collected when antibody titer is 1:256 or greater. Finally, a 1:1 solution is made using serum from each goat, and agglutination with representative red blood cells from a cat, dog, horse, cow, llama and goat is verified to provide the positive control solution 115. In addition, a negative control tube 210 having a negative control solution 215 that cannot agglutinate the blood of any species of mammal used for testing is provided. One possible negative control solution is phosphate buffered saline (PBS). However serum from nonimmunized animals can also be used as the negative control solution as long as it will not cause agglutination of the sample red blood cells. The blood crossmatching test kit 100 can optionally include one or more whole blood dilution tubes 410 having a premeasured volume of low ionic strength saline (LISS) 415 for diluting the whole donor blood. The blood crossmatching test kit can also include one or more reaction tubes 310 for mixing the donor blood and serum of a recipient. Finally, the blood crossmatching test kit 100 can include a number of disposable pipets 510 capable of dispensing drops having a fifty microliter (50 μL) volume.

Figure 5:
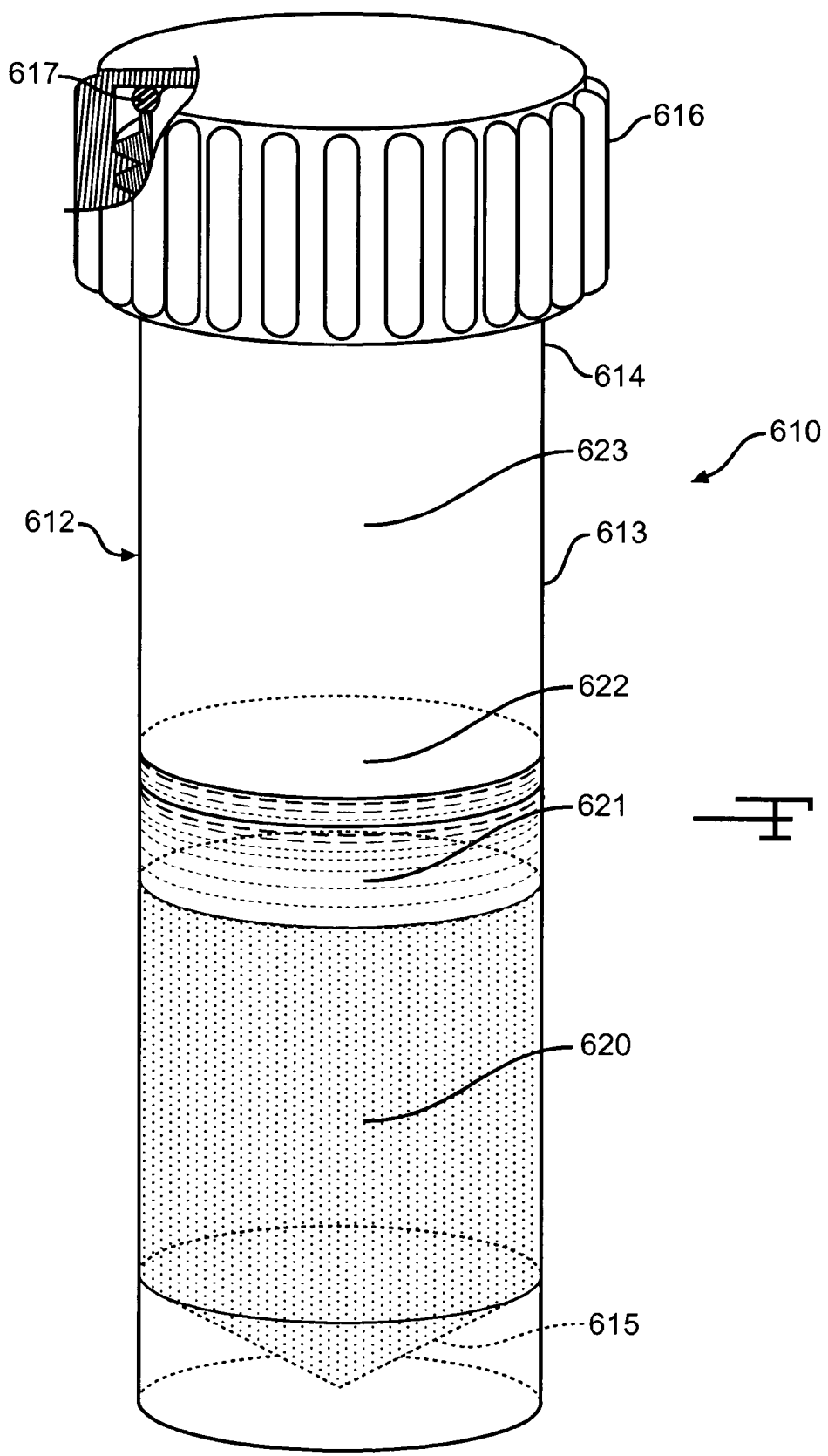
FIG. 5 illustrates another embodiment of a blood crossmatching apparatus 610 of the present invention.

An alternative embodiment of a blood crossmatching apparatus 610 of the present invention is illustrated in FIG. 5. The blood crossmatching apparatus 610 is comprised of a centrifugable tube, such as a microcentrifuge tube 612 for small samples, with an outer wall 613 having an open top end 614 and an opposed closed bottom end 615 defining an internal chamber 623. The bottom end 615 can be conical in shape to make viewing of any precipitated erythrocytes easier. To construct the apparatus 610, a first layer of particulates 620 is layered at the bottom end 615 of the internal chamber 623 in the microcentrifuge tube 612. Next, a density solution is layered over the particulate layer 620 to form a second layer 621. In one (1) embodiment, the density solution of the second layer 621 is an aqueous glycerol solution. However, other aqueous density solutions can be used. Finally, a third layer 622 comprising an immunoglobulin ligand in aqueous solution is floated on the density solution of the second layer 621. In one embodiment, the immunoglobulin ligand is Protein A. The Protein A enhances bridging between red blood cells with weak agglutination. The Protein A also interacts with white blood cells and large proteins (such as albumin) so as to help decrease the amount of white blood cells and protein that enters the first layer 620. The density solution of the second layer 621 separates white blood cells from erythrocytes (ie. red blood cells) in the whole donor blood when the apparatus 610 is centrifuged. Therefore, the crossmatching apparatus 610 can use whole blood to test the compatibility of the mammals for blood transfusion. In the illustrated embodiment, a screw cap 616 is provided with an o-ring 617 to seal the chamber 623 during centrifugation. Any commercially available microcentrifuge tube 612 can be used including, but not limited to, a Sarstedt® brand (Nümbrecht, Germany) microcentrifuge tube.

In one embodiment, the first particulate layer 620 is comprised of 6% agarose particles, optionally Sepharose® 6B beads (GE Healthcare) on the bottom end 615 of the microcentrifuge tube 612. Whole blood can be used with the crossmatching apparatus 610, so washing the erythrocytes is not required. The crossmatching apparatus 610 is dependent upon antigen-antibody interaction of the donor and recipient blood resulting in agglutination. The first particulate layer 620 excludes molecules and antigen-antibody complexes greater than 4,000,000 Daltons (Da) in the case of Sepharose® 6B beads. The first particulate layer 620 acts as a sieve, catching large particles in the upper portion of the first particulate layer 620. The crossmatching apparatus 610 is centrifuged in a standard benchtop centrifuge at a force of about 500×g to about 700×g and the resulting banding pattern is read by evaluating the position of the erythrocytes in the microcentrifuge tube 612 after centrifugation. Positive crossreaction is indicated by a band of erythrocytes in or on the top of the particulate layer 620, while negative crossreaction is indicated by a band of erythrocytes at the bottom end 615 of the microcentrifuge tube 612.

EXAMPLE 1

Figure 6:
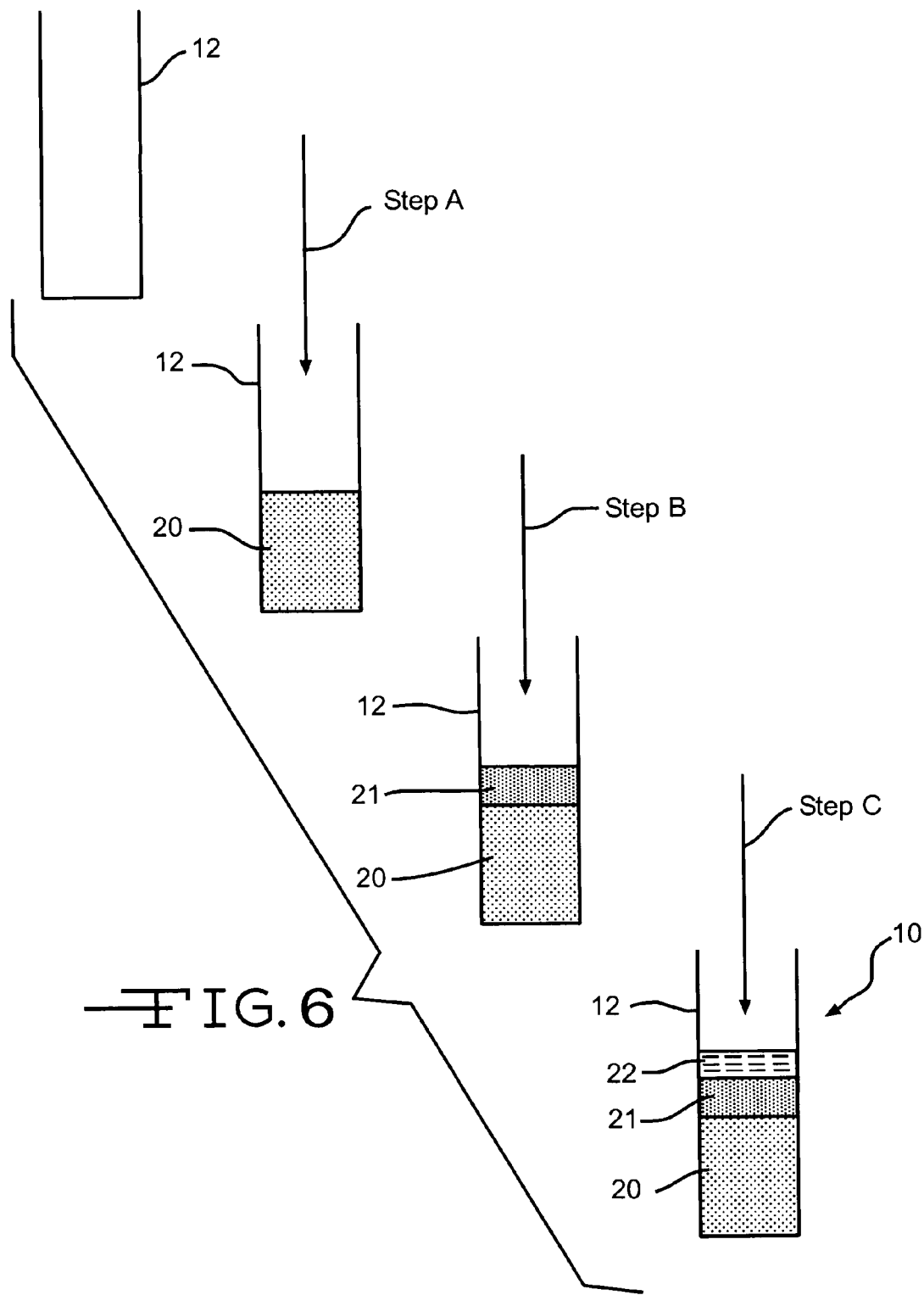
FIG. 6 illustrates a method of preparing the blood crossmatching apparatus 10.

One embodiment of the crossmatching apparatus is prepared in the following manner. Generally, a centrifugeable tube, such as a microcentrifuge tube 12 is provided. FIG. 6 illustrates the steps of forming the layers to provide the apparatus 10. In step (a), a first layer 20 of particulates is layered in the microcentrifuge tube 12. Next, as illustrated in step (b) of FIG. 6, a second layer 21 of particulates is layered upon the first layer 20 in the microcentrifuge tube 12. The second layer 21 of particulates has immunoglobulin ligands, such as Protein A, bound to the particulates. Finally, as illustrated in step (c) of FIG. 6, a density solution 22 is layered over the second layer 21 to provide the apparatus 10. Steps (a) through (c) are described further in the detailed embodiment of the following paragraph.

In step (a), one milliliter (1 mL) of Sepharose 6B® beads (commercially available 6% agarose beads) is pre-heated to 56° C. and then layered into the bottom of a microcentrifuge tube 12 as a first particulate layer 20. Pre-heating to 56° C. allows the Sepharose 6B® beads to flow better when layering the beads into the microcentrifuge tube 12. The microcentrifuge tube 12 is then incubated at about 4-6° C. for between about twelve to twenty-four (12-24) hours. The microcentrifuge tube 12 is brought to room temperature after this incubation. In step (b), fifty microliters (50 µL) of phosphate buffer saline (PBS) and Protein A stabilized on 250 micron (µm) acrylic beads is layered as a second particulate layer 21 onto the solid gel matrix of the first particulate layer 20. The microcentrifuge tube 12 is then allowed to stabilize for thirty (30) minutes. In step (c), fifty microliters (50 µL) of a ninety seven percent (97% v/v) glycerol density solution 22 is layered on top of the particulate layers 20, 21. The tube 12 is then incubated again at about 4-6° C. for between about twenty four to thirty six (24-36) hours. However, it is to be understood that the duration and temperature of each of the incubation steps can be varied to some extent without substantially impacting the performance of the apparatus. The solid particulate matrix of the particulate layers 20, 21 of the apparatus 10 is capable of withstanding temperatures in the range of 4-32° C. without changing its ability to perform. Allowing the first particulate layer 20 and the second layer of particulates 21 to stabilize and settle increases the structure of the first and second layers 20 and 21 and allows the layers 20 and 21 to withstand centrifugation at high speeds without the first and second layers 20 and 21 becoming intermingled.

EXAMPLE 2

The following example describes one possible procedure that can be used to perform a cross matching assay using the blood crossmatching kit and apparatus of the present invention. While the example describes using the apparatus for major crossmatching, it is to be understood that the apparatus of the present invention can also be used for minor crossmatching.

Sample Collection: Collect one half milliliter (0.5 mL) of ethylenediaminetetraacetic acid (EDTA) treated whole blood from the donor mammal or locate a segment from previously collected donor packed red blood cells. The whole blood is collected and treated with EDTA by methods known in the art. Collect one milliliter (1.0 mL) of serum from the recipient mammal. It is recommended to collect at least 2.5 mL of whole blood from the recipient mammal and then centrifuge to separate the blood and provide the serum. Place the serum into a separate tube.

Dilution of donor blood: Remove the materials provided in the kit 100, including the apparatus 10, the positive control tube 110 with the positive control solution 115, the negative control tube 210 having the negative control solution 215, the whole blood dilution tube 410 having the premeasured volume of low ionic strength saline (LISS) 415, the reaction tubes 310, and the disposable pipets 510. Using one of the disposable pipets 510 that deliver fifty microliter (50 µL) drops, add one half milliliter (0.5 mL, ie. ten drops) of EDTA whole blood (or packed red blood cells from the blood bag segment) to the four and a half milliliters (4.5 mL) of low ionic strength saline (LISS) 415 in a tube 410 labeled as "whole blood mix". For example, a fifteen milliliter (15 mL) tube can be used. Label the "whole blood mix" tube 410 with the donor name. Invert the whole blood mix tube 410 several times to mix thoroughly.

Mixing and reaction: Remove the positive control solution tube 110, the negative control solution tube 210 and the reaction tube 310 and place into the rack. Label the reaction tube 310 with the donor name. Place two hundred microliters (200 µL, ie. four drops) of recipient serum into the reaction tube 310, using one of the pipets 510. Using a separate pipet 510, place one hundred microliters (100 µL, ie. two drops) of the donor "whole blood mix" into the same reaction tube 310, and mix well. This is the sample blood/serum mixture 40. Place one hundred microliters (100 µL, ie. two drops) of the donor "whole blood mix" into the positive control solution tube 110 and mix well. Place one hundred microliters (100 µL, ie. two drops) of the donor "whole blood mix" into the negative control tube 210 and mix well. Incubate all of the tubes 110, 210, 310 for five minutes.

Centrifugation: Dispense an aliquot of fifty microliters (50 µL, ie. one drop) of the sample blood/serum mixture 40 from the reaction tube 310 into a blood crossmatching apparatus 10. Label the apparatus 10 with the donor name. Transfer fifty microliters (50 µL, ie. one drop) of the blood/serum mixture 40 from the positive control reaction tube 110 into a blood crossmatching apparatus 10. Label the apparatus 10 with a positive sign (+). Transfer fifty microliters (50 µL, ie. one drop) of the blood/serum mixture 40 from the negative control reaction tube 210 into a blood crossmatching apparatus 10. Label the apparatus 10 with a negative sign (−). Place the three labeled blood crossmatching apparatuses 10 into a centrifuge and spin according to the speeds listed in Table 1 to achieve approximately from 500×g to 700×g.

TABLE 1

Centrifuges speed settings.

| Centrifuge model | Speed | Time |
|---|---|---|
| StatSpin ® MP<br>Iris Sample Processing<br>(Westwood, MA) | 9800 rpm<br>(urine setting) | 45 seconds |
| Triac ™<br>Becton Dickinson<br>(Franklin Lakes, NJ) | 3800 rpm<br>(serum setting) | 7 minutes |
| SeroFuge ®<br>Becton Dickinson<br>(Franklin Lakes, NJ) | 3400 rpm | 5 minutes |
| Clay Adams ™<br>Becton Dickinson<br>(Franklin Lakes, NJ) | 3200 rpm | 5 minutes |

Interpretation: The positive and negative control results can be interpreted as illustrated in FIG. 3A-D. The positive control banding pattern should demonstrate a ring of red blood cells at the top of the first particulate layer as illustrated in FIG. 3A. The negative control banding pattern should demonstrate a ring of red blood cells at the bottom of the first particulate layer 20 as illustrated in FIG. 3C. Interpret the reaction in the sample blood crossmatching apparatus by matching with one of the possible banding pattern outcomes as illustrated in FIG. 3A-D. A positive test is considered any apparatus 10 demonstrating red blood cells (erythrocytes 42) at the top of the first particulate layer 10 after centrifugation (FIGS. 3A,B). In weak (2+) agglutination, some of the cells 42 can be trapped at the top while some end up in the upper portion of the first particulate layer 20 (FIG. 3B). A negative test is considered any apparatus 10 with red blood cells 42 at the bottom of the first particulate layer 20 after centrifugation (FIGS. 3C,D). High hematocrits can yield a negative result that demonstrates an "arrow" appearance at the bottom of the apparatus 10 (FIG. 3D). Record the test results. Use the positive and negative control tubes 110, 210 to provide on site examples of possible banding patterns. A positive crossmatch indicates the recipient is at risk for demonstrating a transfusion reaction. Therefore, this donor must not be used for transfusion. A negative crossmatch indicates the recipient is not at risk for demonstrating a transfusion reaction. Therefore, this donor can be used for transfusion.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:

1. A blood crossmatching apparatus for testing compatibility of mammals for blood transfusion using whole blood comprising:
    (a) a centrifugeable tube having an open top end and an opposed closed bottom end;
    (b) a first layer of particulates at the bottom end in the centrifugeable tube having a permeability enabling nonagglutinated red blood cells of compatible mammals to pass through the layer;
    (c) a second layer of particulates layered upon the first layer in the centrifugeable tube, wherein particulates of the second layer comprise an immunoglobulin ligand bound to the particulates for bridging weakly agglutinating red blood cells; and
    (d) a density solution layered into the centrifugeable tube over the second layer, wherein the density solution separates white blood cells from red blood cells in the whole blood when centrifuged, such that the apparatus can show an incompatibility of the mammals for blood transfusion as a red blood cell band on or in an upper portion of the first layer.

2. The blood crossmatching apparatus of claim 1, wherein the centrifugeable tube is a microcentrifuge tube or a microhematocrit capillary tube.

3. The blood crossmatching apparatus of claim 1, wherein the first layer of particulates comprises 6% agarose particles.

4. The blood crossmatching apparatus of claim 1, wherein the second layer of particulates comprises 250 micron (μm) acrylic beads.

5. The blood crossmatching apparatus of claim 1, wherein the density solution comprises an aqueous glycerol solution.

6. The blood crossmatching apparatus of claim 5, wherein the aqueous glycerol solution comprises a 97% v/v glycerol solution.

7. The blood crossmatching apparatus of claim 1, wherein the immunoglobulin ligand is Protein A.

8. The blood crossmatching apparatus of claim 1, wherein the density layer has a depth from about 0.05 mm to about 1.5 mm.

9. A method of making a blood crossmatching apparatus for testing compatibility of mammals for blood transfusion using whole blood comprising the steps of:
    (a) providing a centrifugeable tube having an open top end and an opposed closed bottom end;
    (b) forming a first layer of particulates at the bottom end in the centrifugeable tube;
    (c) forming a second layer of particulates upon the first layer in the centrifugeable tube, wherein particulates of the second layer comprise an immunoglobulin ligand bound to the particulates; and
    (d) layering a density solution over the second particulate layer, wherein the density solution separates white blood cells from red blood cells in the whole blood when centrifuged so that the apparatus can show an incompatibility of the mammals for blood transfusion as a red blood cell band on or in an upper portion of the first layer.

10. The method of claim 9 further comprising the steps of: incubating the centrifugeable tube at about 4-6° C. for between about twelve to twenty-four (12-24) hours after forming the first layer of particulates in step (b).

11. The method of claim 10 further comprising the steps of: bringing the centrifugeable tube to room temperature after the incubating.

12. The method of claim 9 further comprising the steps of: incubating the centrifugeable tube for about thirty (30) minutes after forming the second layer of particulates upon the first layer in step (c).

13. The method of claim 9 further comprising the steps of: incubating the centrifugeable tube at about 4-6° C. for between about twenty four to thirty six (24-36) hours after layering the density solution over the second layer in step (d).

* * * * *